United States Patent
Melrose et al.

(10) Patent No.: US 6,410,040 B1
(45) Date of Patent: Jun. 25, 2002

(54) POLYMERIC COMPOUNDS AND METHODS OF FORMULATING SAME

(75) Inventors: Graham John Hamilon Melrose, Dalkeith; Andrew James Huxham, Balga, both of (AU)

(73) Assignee: Chemeq Limited, Bentley (AU)

( * ) Notice: Subject to any disclaimer, the term of this patent is extended or adjusted under 35 U.S.C. 154(b) by 0 days.

(21) Appl. No.: 09/701,311

(22) PCT Filed: Jul. 16, 1999

(86) PCT No.: PCT/AU99/00578

§ 371 (c)(1),
(2), (4) Date: Nov. 28, 2000

(87) PCT Pub. No.: WO00/03723

PCT Pub. Date: Jan. 27, 2000

(30) Foreign Application Priority Data

Jul. 17, 1998 (AU) .............................................. PP 4719
Aug. 10, 1998 (AU) ............................................ PP 5167

(51) Int. Cl.$^7$ .......................... A01N 25/00; A61K 7/00; A61K 7/42; A61K 31/74

(52) U.S. Cl. ...................... 424/404; 424/59; 424/78.02; 424/78.08; 424/400; 424/401

(58) Field of Search .......................... 424/59, 400, 401, 424/404, 78.02, 78.08

(56) References Cited

FOREIGN PATENT DOCUMENTS

| AU | 9511686 | 8/1995 |
|---|---|---|
| WO | WO 88/04671 | 6/1988 |
| WO | WO 96/38186 | 12/1996 |

*Primary Examiner*—Shelley A. Dodson
(74) *Attorney, Agent, or Firm*—Rothwell, Figg, Ernst & Manbeck

(57) ABSTRACT

A method for the preparation of compositions of poly(2-propenal, 2-propenoic acid) comprising the method steps of dissolving the poly(2-propenal, 2-propenoic acid) in aqueous base, adding an organic compound containing one or more hydrophobic groups, and subsequently acidifying the solution, whereby interaction between the hydrophobic groups of the organic compound and the poly(2-propenal, 2-propenoic acid) prevents precipitation of the poly(2-propenal, 2-propenoic acid) occurring at pH >5.5 and the solution is consequently stable over a broad pH range.

28 Claims, No Drawings

POLYMERIC COMPOUNDS AND METHODS OF FORMULATING SAME

FIELD OF THE INVENTION

The present invention relates to polymeric compounds and methods of formulating same, said polymeric compounds having a polyacrolein sub-unit in aldehyde, hydrated, hemi-acetal or acetal form and having biostatic or biocidal properties. More particularly, the present invention is directed to compositions containing the above noted polymeric compounds and the biostatic and/or biocidal uses of these compositions.

BACKGROUND ART

The broad-based antimicrobial properties of polymers having the repeating polymeric unit:

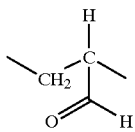

or this unit in its hydrated, hemi-acetal or acetal form, represented by the formulae:

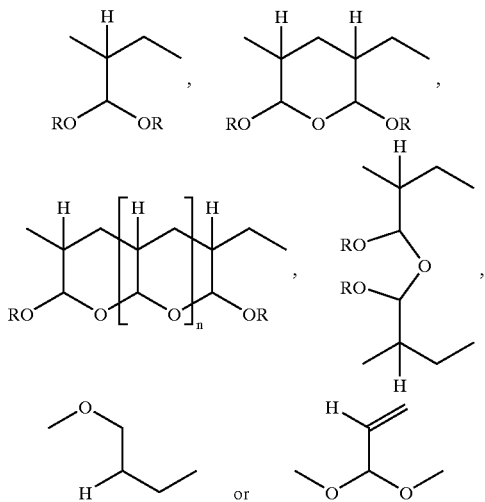

wherein R is hydrogen or alkyl and n is an integer of one or more have been demonstrated previously (International Patent Application Publication WO 88/04671). The compounds particularly described therein include poly(2-propenal, 2-propenoic acid).

It has also been noted previously (International Patent Application Publication WO 96/38186) that poly(2-propenal, 2-propenoic acid) is formed when the aldehyde groups of poly (2-propenal) syn polyacrolein are partially auto-oxidised to carboxyl groups. It was further noted that the polymer is soluble in dilute aqueous bases, for example aqueous sodium carbonate.

It is known that antimicrobial compositions may be used as preservatives, or as the active ingredients in disinfectants, dermatological compositions including sun screen formulations or antiseptic formulations, or in animal feed additives.

Generally these antimicrobial compositions must:
be stable;
be efficacious in killing micro-organisms within a specified time;
be safe, that is be reasonably free of toxicity which may be caused by the trans-dermal migration of low molecular weight ingredients into the blood-stream so as to manifest toxicity, antigenicity, allergy, irritation or inflammation;

have minimal odour; and in some dermatological preparations, have the property of sun screening and minimise adverse dermatological sffects from the generation of free-radicals.

Specifically, antimicrobial formulations applied to inanimate objects and the skin are usually termed disinfectants and antiseptics, respectively. Often, regulatory standards demand that a disinfectant formulation first, is stable and secondly, kills a chosen quantum of vegetative micro-organisms within 10 minutes. That is, the antimicrobial activity of these compositions must be biocidal and quick. The formulations described herein are substantially aimed at these goals, but often achieve more, for example killing even extremely resistant bacterial spores within the frequent standard of 24 hours.

Formulation of poly(2-propenal, 2-propenoic acid) simply by dissolution in dilute aqueous sodium carbonate, and then neutralisation to pH 7, has now been found to provide a composition that does not always kill micro-organisms fast enough to meet the above standards.

It is one object of the present invention to provide methods of preparing compositions containing compounds of the type described by the prior art and in particular poly(2-propenal, 2-propenoic acid), and which are useful disinfectants and/or antiseptics meeting these standards.

It is a further object of the present invention to provide a method of preparing polymers and/or copolymers derived from acrolein in accordance with the above mentioned prior art for use as useful disinfectants and/or antiseptics.

It is a still further object of the present invention to provide a method of preparing polymers and/or copolymers derived from acrolein in accordance with the above mentioned prior art, for use in dermatological formulations, including sunscreens.

It is yet still a further object of the present invention to provide a method of preparing polymers and/or copolymers derived from acrolein in accordance with the above mentioned prior art for use in other applications including as a preservative or as an animal feed-additive.

Throughout this specification, unless the context requires otherwise, the word "comprise", or variations such as "comprises" or "comprising", will be understood to imply the inclusion of a stated integer or group of integers but not the exclusion of any other integer or group of integers.

DISCLOSURE OF THE INVENTION

In accordance with the present invention there is provided a method for the preparation of compositions of poly(2-propenal, 2-propenoic acid) comprising the method steps of dissolving the poly(2-propenal, 2-propenoic acid) in aqueous base, adding an organic compound containing one or more hydrophobic groups, and subsequently acidifying the solution, whereby interaction between the hydrophobic groups of the organic compound and the poly(2-propenal, 2-propenoic acid) prevents precipitation of the poly(2-propenal, 2-propenoic acid) occurring at pH $\geq 5.5$ and the solution is consequently stable over a broad pH range.

Preferably, the precipitation of the poly(2-propenal, 2-propenoic acid) is prevented at pH $\geq 3.5$.

The organic compound may be an anionic surfactant. The anionic surfactant is preferably selected from either sodium lauryl sulphate or disodium decyl (sulfophoxy) benzene sulfonate and disodium oxybis (decylsulfophenoxy) benzene sulfonate.

In one form of the invention, one or more phenols may be added to the solution of poly(2-propenal, 2-propenoic acid) prior to acidification. The phenol is preferably o-phenyl-phenol.

In a further form of the invention, the composition containing poly(2-propenal, 2-propenoic acid) is firstly stored for a time in basic composition prior to addition of surfactant and acidification.

In a still further form of the invention, the composition exhibits increased antimicrobial activity, the method of preparing the composition comprising preparation of the poly(2-propenal, 2-propenoic acid) in the presence of air and/or oxygen, with or without inhibitor. Alternately, the method comprises the subsequent making of the composition of poly(2-propenal, 2-propenoic acid) into a basic composition.

Preferably, the organic compound is one or more of ethylene diamine tetra acetic acid, a lower alkanol, a phenol, isothiazolinones and glutaraldehyde, the composition exhibiting a synergistic increase in antimicrobial activity.

The composition may further comprise phenols and/or glutaraldehyde, whereby the odour of the phenols and/or glutaraldehyde is reduced by the presence of the poly(2-propenal, 2-propenoic acid).

The composition may exhibit reduced trans-dermal migration of low molecular weight components of the composition as a result of the presence of poly(2-propenal, 2-propenoic acid). The low molecular weight composition may contain a sunscreen agent. The sunscreen agent may be either or both of octyl methoxy cinnamate and octyl dimethyl p-aminobenzoate.

In one form of the invention, the composition, especially for dermatological use, exhibits a sunscreening effect as a result of the presence of poly(2-propenal, 2-propenoic acid).

In another form of the invention, the composition exhibits the formation of a continuous antimicrobial film on substrates.

In another form of the invention, the composition, especially for dermatological use exhibits a free-radical scavenging effect as the result of the presence of poly(2-propenal, 2-propenoic acid).

In accordance with the present invention there is provided an aqueous polymeric composition comprising poly(2-propenal, 2-propenoic acid) and an organic compound containing one or more hydrophobic groups, wherein interaction between the hydrophobic groups of the organic compound and the poly(2-propenal, 2-propenoic acid) prevents the precipitation of the poly(2-propenal, 2-propenoic acid) at pH >5.5.

Preferably, the poly(2-propenal, 2-proppnoic acid) does not precipitate at a pH 2 3.5.

Still preferably, the organic compound is an anionic surfactant. The anionic surfactant may be chosen from either sodium lauryl sulphate or disodium decyl (sulfophoxy) benzene sulfonate and disodium oxybis (decylsulfophenoxy) benzene sulfonate.

The composition may further comprising one or more phenol. The phenol may be o-phenyl-phenol.

In one form of the invention, the composition further comprises one or more of ethylene diamine tetra acetic acid, a lower alkanol, a phenol, isothiazolinones and glutaraldehyde, the composition exhibiting a synergistic increase in antimicrobial activity.

The composition may be an emulsion.

In accordance with the present invention there is still further provided the use of the above defined compositions for antimicrobial uses, for dermatological uses, or for use as a feed additive.

BEST MODE(S) FOR CARRYING OUT THE INVENTION

It has now been discovered that modifying the preparation of poly(2-propenal, 2-propenoic acid) as described in both WO 88/04671 and WO 96/38186 (Example 1b in each) by concurrently bubbling in air and/or oxygen during the polymerisation, produces a polymer with more discreet crystalline form which aids recovery and subsequent drying, and in solid or in liquid medium has less contaminating and slightly odorous oligomers, and has higher inherent rate of antimicrobial activity; see Example 1 hereinafter.

It has now been found that whilst basic aqueous compositions containing the poly(2-propenal, 2-propenoic acid) are biostatic and/or biocidal; nevertheless, the compostions are appreciably unstable. Although, it has further been shown that lowering the pH (lowering the hydroxyl ion concentration) of such compositions/solutions increases their chemical stability, counter-productively, it has been found that acidification of the composition to pH's below approximately pH 6, causes precipitation of the poly(2-propenal, 2-propenoic acid).

It has now been shown that this precipitation can be avoided until approximately pH 3.5 (ie. over ten-fold, less hydroxyl ion concentration), by a method of formulating in which the poly(2-propenal, 2-propenoic acid) is first dissolved in dilute aqueous base, then anionic surfactant added, before the acidification. Useful anionic surfactants are either sodium lauryl sulphate ("SLS") or disodium decyl (sulfophoxy) benzene sulfonate and disodium oxybis (decylsulfophenoxy) benzene sulfonate in equal weight ratios with the poly(2-propenal, 2-propenoic acid). To be effective, it is important to maintain this order of addition, so that the poly(2-propenal, 2-propenoic acid) is in its anionic form before the addition of the surfactant; see Example 2 hereinafter. This apparent interrelationship between the two negatively charged species from poly(2-propenal, 2-propenoic acid), and anionic detergent is surprising since repulsion between the like-charges on the species would be expected.

It has now been found that basic aqueous solutions of poly(2-propenal, 2-propenoic acid) kill micro-organisms more rapidly than do acidic solutions of the polymer. This discovery led to the further finding that formulations of more stable, acidic compositions containing poly(2-propenal, 2-propenoic acid) and preferably, anionic surfactant, could subsequently be made basic and hence, more antimicrobially active, immediately before use as, for example, either a disinfectant and/or antiseptic and/or preservative; see Example 10 hereinafter.

It has now been shown that if a solution of poly(2-propenal, 2-propenoic acid) which contains a phenol, with anionic surfactant is acidified, a surprisingly stable emulsion is formed, and in this heterogenous system, the poly(2-propenal, 2-propenoic acid) in the hydrophobic phase is protected from chemical degradation by the hydroxyl ions in the hydrophilic phase; see Example 2 hereinafter. o-Phenyl-phenol is particularly useful, and in equal weight ratio with the poly(2-propenal, 2-propenoic acid).

It has now been shown that the inclusion of phenols additionally to anionic surfactants in compositions containing poly(2-propenal, 2-propenoic acid) allows further acidification of these compositions before any precipitation of the poly(2-propenal, 2-propenoic acid) ie. further chemical stability with respect to hydroxyl ion and/or base is achieved; see Example 2 hereinafter. Further, it has now been shown that if the composition containing poly(2-propenal, 2-propenoic acid) only is firstly stood, for example for about 11 days at about pH 9, in an aqueous alkaline medium, before the addition of the anionic surfactant and then phenol-precipitation will not occur at all, upon acidification; see Example 2 hereinafter.

It has now been shown that co-formulation of the composition containing poly(2-propenal, 2-propenoic acid), with anionic surfactant, and optionally with additionally a phenol, produces a composition which provides a continuous antimicrobial film upon substrates, after application thereto, eg. skin, flooring, walls furniture etc. Without these additives, the film is invariably discontinuous and hence only partially protects the substrate, antimicrobially. It has now been shown that these films retain moisture, facilitating their protective antimicrobial activities. If they also contain a volatile component which effects their pH-dependent antimicrobial activities, then, in turn, these activities may be increased as evaporation takes place; see Example 10 hereinafter.

It has now been shown that inclusion of anionic surfactant in formulations containing poly(2-propenal, 2-propenoic acid), increases their chemical stability to hydroxyl ion and/or base; see Example 3 hereinafter.

It has now been shown that poly(2-propenal, 2-propenoic acid) absorbs in the UV, and that a peak about 268 nm, as it is replaced by absorption at approximately 232 nm, correlates with and is a convenient monitor of the chemical stability of poly(2-propenal, 2-propenoic acid) in basic aqueous solutions; see "Stability Test" hereinafter.

It has now been shown that co-formulating anionic surfactant and/or ethylenediaminetetraacetic ("EDTA") acid and/or its salts and/or a lower alkanol enhances the antimicrobial properties of compositions containing the poly(2-propenal, 2-propenoic acid); see Examples 4 and 5 hereinafter.

It has now been shown, further, that not only is the antimicrobial activity increased—but surprisingly, it is synergistically increased by incorporating in the compositions containing the poly(2-propenal, 2-propenoic acid) either, EDTA (and/or its salts), and/or phenols, and/or isothiazolinones, and/or glutaraldehyde; see Example 7 hereinafter.

It has now been shown that inclusion of poly(2-propenal, 2-propenoic acid) decreases the notorious odours of compositions containing antimicrobial phenol(s) and/or glutaraldehyde; see Example 6 hereinafter.

It has now been shown that the surprising apparent interaction between the negatively-charged phenols and the negatively-charged anionic form of poly(2-propenal, 2-propenoic acid) is more general, and is thought to result from the interaction of the hydrophobic portions of the respective species. Thus, the presence of poly(2-propenal, 2-propenoic acid) in an emulsion with the UV sunscreen octyl methoxy cinnamate, or octyl dimethyl p-aminobenzoate, is shown to prevent the migration of either of the sunscreens through a membrane which is a model for the skin; see Example 8 hereinafter. Hence, it is apparent that poly(2-propenal, 2-propenoic acid) may be used as a co-formulant to reduce potential toxicity and/or allergy and/or antigenicity and/or irritation and/or inflammation from sunscreen agents, or other compounds, eg. phenols, which results from trans-dermal migration of such constituents, in dermatological preparations, into the bloodstream.

It has been shown further, that the peak at 268 nm and below provides significant UVC absorption. UVC energy is greater than 50% of the energy in sunlight (Lide, D. R., "CRC Handbook of Chemistry and Physics", CRC Press, 73rd edition, 1992–93, page 14–8) and is in the wavelength to which the skin is most sensitive ("Harry's Cosmeticology", J. B. Wilkinson and R. J. Moore Eds., Chemical Publishing Co. Inc., New York, 1982, page 228) and which induces changes that alter the structure of DNA (Kano R. J. and Colome J. S. "Microbiology", West Publishing Company, 1986, page 162). Thus, it has now been found that it is an advantage to include poly(2-propenal, 2-propenoic acid) in dermatological sunscreen preparations.

It has now been shown that compositions containing poly(2-propenal, 2-propenoic acid) and containing only polymeric ingredients (eg. polymeric solvents/emollients and/or polymeric surfactants and/or emulsifiers) and/or volatile ingredients provide compositions for dermatological applications, free of any components which, after spreading on the skin, may migrate trans-dermally and into the bloodstream to cause toxicity, allergy etc; see Example 8 hereinafter.

It has now been shown that the formulation of such compositions (eg free of conventional surfactants) is facilitated by the surfactant properties of poly(2-propenal, 2-propenoic acid).

It has now been shown that poly(2-propenal, 2-propenoic acid) has the capacity to absorb free-radicals and this is a distinct use in dermatological compositions with a view to minimising skin-damage brought about by free-radicals; see Example 9 hereinafter.

It has now been shown that the methods, compnositions and uses provided herein, apply to all compounds described in WO 88104671 and WO 96138186, particularly those compounds which are hydrophilic and/or soluble in aqueous media; the methods shown herein of keeping these compounds in solution and/or emulsion in aqueous media generally facilitate any desired chemical reactions with these compounds in acidic media.

The invention will now be described with reference to a number of specific Examples, each of which should not be construed as limiting the scope of the invention. In the following examples, reference is made to a number of tests as follows:

1. Biocidal Test

Dilute sample with sterile water to obtain required concentration. Weight 1 9.9 g of diluted sample into a sterile jar and inoculate with 0.1 mL of $10^7$–$10^8$ suspension of Ps. aeruginosa and mix. Immediately transfer 1 mL of inoculated sample to 9 mL of letheen broth and vortex. Plate out serial 1 in 10 dilutions. Pour with tryptone soya agar. Incubate 3 days at 37° C.

2. Minimal Kill Concentration Test

Make serial 1 in 2 dilutions of the sample using sterile 0.85% saline. Add 0.1 mL of suspension of test organism to the dilution. Incubate at 37° C. for 24 hours. Subculture 1 mL from each tube into 10 mL sterile nutrient broth plus TWEEN 80; incubate at 37° C. for 24 hours.

3. Sporicidal Test

Add 1 mL of spore suspension of B. subtilus var niger (cfu $10^7$/mL) to 10 mL of solution of the sample in a sterile bottle, and vortex. Immediately remove 0.020 mL and add to recovery broth; repeat 5 times. Vortex and incubate at 37° C. for 14 days. Confirm by "heat shock" to all tests.

4 Sporicidal Efficacy Test

Inoculate sterile glass slides with a suspension of B. subtilus var niger (cfu $10^7$/mL). Dry under vacuum for 24 hours at 30° C. Add 4 mL sample solution to slide. After 10 min contact time, dry slides at 30° C. for 72 hours. Sonicate and vortex slides into deactivation broth. Enumerate by performing 4 serial 1 in 10 dilutions in agar and incubate for 48 hours at 30° C.

5. Modified Kelsey Svkes Test

Add 1 mL of culture of test organism ($2 \times 10^8$–$2 \times 10^9$) cfu/mL containing 1% yeast to 3 mL of test solution. At 8 minutes, subculture 0.02 mL into each of 5 tubes containing recovery broth, and vortex. Incubate at 37° C. for 48 hours.

6. Stability Test

Poly(2-propenal, 2-propenoic acid) (1 g) was dissolved in 0.5% w/w aqueous sodium carbonate, and stood at room temperature. The stability was measured by the UV method.

The stability of aqueous solutions of polymers were followed by the disappearance of a UV peak near 268 nm, and the appearance of a peak near 232 nm; ca. absorbance at 268 nm, of 0.02% solution=1.5.

EXAMPLE 1

(a) With hydroquinone: open to air

Water (720 mL at ambient temperature, about 20° C.) and acrolein (60 g; freshly distilled and hydroquinone added to 0.25% w/w) were placed in an open beaker, within a fume cupboard, and very vigorously stirred, mechanically. Then, 0.2 M aqueous sodium hydroxide (21.4 mL) was added to bring the pH to 10.5–11.0. The solution immediately turned a yellow typical of the hydroquinone anion and, within a minute, the colour had disappeared and the clear solution became milky. About 1 minute later, precipitation of a white crystalline, flocculent polymer began, and appeared complete within 15–30 minutes. The polymer precipitate, poly (2-propenal, 2-propenoic acid), was filtered and washed with water (250 mL), dried at room temperature upon filter papers for 2 days (yield 25.2 g), then spread as a thin layer in glass petri dishes and heated at 40° C./8 hours. This heating was continued at the following schedules: 50° C./15 hours (then ground), 65° C./4 hours, 70° C./2 hours, 75° C./18 hours, 82° C./24 hours. It is envisaged that this method may be scaled-up to include, eg. the stepwise addition of acrolein, followed by more rapid drying.

Typically a solution of the resulting poly(2-propenal, 2-propenoic acid) was prepared by adding 2 g, with stirring over 15–30 minutes, to a 1% w/w aqueous sodium carbonate solution (100 mL) and diluted as required.

(b) With hydroquinone; closed vessel

As above for (a) except the reaction vessel was a stoppered 1 litre flask; this resulted in a slowly-forming precipitate which was glassy and poorly crystalline-yield 25.5 g.

(c) Without hydroquinone; closed vessel

As above for (a), except hydroquinone was excluded, and the reaction vessel was a stoppered 1 litre flask; this resulted in a crystalline product—yield 21.0 g.

(d) Without hydroquinone; open to the air

As above for (a), except hydroquinone was excluded; this resulted in a crystalline product—yield 26.0 g.

After 3 days at room temperature, the diluted samples (0.25% w/w), being the product of examples 1(a) to 1(b), were tested by the Biocidal Test. The results are shown in Table 1:

TABLE 1

| | cfu/mL (i.e. Colony forming units/ml) | | | |
|---|---|---|---|---|
| Sample | 1 minute | 5 minutes | 15 minutes | 30 minutes |
| 1 (a) | $6.6 \times 10^5$ | $1.6 \times 10^5$ | 50 | 0 |
| 1 (b) | $7.7 \times 10^5$ | $4.7 \times 10^5$ | $8.2 \times 10^3$ | 0 |
| 1 (c) | $9.0 \times 10^5$ | $8.1 \times 10^5$ | $6.2 \times 10^3$ | 0 |
| 1 (d) | $8.3 \times 10^5$ | $2.1 \times 10^5$ | 60 | 0 |

EXAMPLE 2

A series of tests were conducted to examine the impact of surfactant, and/or water, and/or buffer, and/or phenol on precipitation state and pH. Results are shown in Table 2:

TABLE 2

| Polymer | Surfactant | Water | Buffer | Phenol | Observation at 3 days | pH at precipitation |
|---|---|---|---|---|---|---|
| 10 mL A | — | 2 mL | 4 mL I | — | heavy precipiate | 5.5 |
| 10 mL A | 0.4 g C | — | 4 mL I | — | clear | 3.5 |
| 10 mL A | 0.4 g D | — | 4 mL I | — | clear | 3.5 |
| 10 mL B | 0.4 g D | — | 4 mL I | — | clear | <3.5 |
| 10 mL A | 0.4 g E | — | — | — | clear | <3.5 |
| 10 mL A | 0.4 g E | — | — | 0.2 g F | emulsion | <3.5 |
| 10 mL A | 0.4 g E | — | — | 0.4 g G | emulsion | <3.5 |
| 10 mL A | 0.4 g E | — | — | 0.4 g H | emulsion | <3.5 |

A 4% w/w polymer in 4% w/w sodium bicarbonate, freshly prepared.
B as A, aged for 11 days at room temperature.
C Aqueous 4% w/w sodium lauryl sulphate.
D Aqueous 4% w/w Dowfax 3B2.
Decyl (sulfophenoxy) benzenesulfonic acid, disodium salt.
Oxybis (decylbenzenesulfonic acid), disodium salt.
E Dowfax 3B2 - Aqueous 4% w/w Dowfax 3B2.
Decyl (sulfophenoxy) benzenesulfonic acid, disodium salt.
Oxybis (decylbenzenesulfonic acid), disodium salt.
F Dowicide A - orthophenylphenol, sodium salt.
G Dowicide (orthophenylphenol), 33% w/w, in sodium hydroxide solution, 66% w/w.
H 4-tert-amylphenol, 33% w/w, in sodium hydroxide solution, 66% w/w.
I 10% w/w acetic acid: sodium hydroxide buffer, pH 4.5.

EXAMPLE 3

(a) A solution of 2% w/w poly(2-propenal, 2-propenoic acid) in 2% w/w aqueous sodium carbonate containing 2% w/w sodium lauryl sulphate at ambient pH (~9.8) was shown by the UV test to be more stable than a solution without the sodium lauryl sulphate over 11 days/38° C.

(b) A solution of 4% w/w poly(2-propenal, 2-propenoic acid) in 4% w/w aqueous sodium bicarbonate containing 2% w/w sodium lauryl sulphate, acidified with hydrochloric acid to pH5, was shown by the UV test to be more stable than a solution without the sodium lauryl sulphate over 4 days/room temperature.

Results are shown in Table 3:

TABLE 3

| | Sodium Lauryl | | Absorbance Ratio $A_{232}/A_{268}$ | | |
|---|---|---|---|---|---|
| Sample | Sulphate (2% w/w) | pH | 0 hrs | 96 hrs | 264 hrs |
| 3(a) | No | 9.8 | 0 | — | ∞ |
| 3(a) | Yes | 9.8 | 0 | — | 1.36 |
| 3(b) | No | 5.0 | 0 | 1.05 | — |
| 3(b) | Yes | 5.0 | 0 | 0 | — |

EXAMPLE 4

A series of tests were conducted to examine the impact of the incorporation of EDTA or SLS on the antimicrobial activity of a 2% w/w solution of poly(2-propenal, 2-propenoic acid). Results of the Biocidal Test are shown in Table 4:

TABLE 4

| Sample | cfu/mL | | | |
|---|---|---|---|---|
| | 1 minute | 5 minutes | 15 minutes | 30 minutes |
| Control | $3.7 \times 10^6$ | $5.1 \times 10^6$ | $9.2 \times 10^4$ | 0 |
| plus EDTA (0.25%) | $3.7 \times 10^6$ | 0 | 0 | 0 |
| plus SLS (0.25%) | $3.7 \times 10^6$ | $2.7 \times 10^6$ | 0 | 0 |

EXAMPLE 5

A test formulation of 1.5% w/w solution of poly(2-propenal, 2-propenoic acid) in 65% wow ethanol in water was compared with a control formulation of 65% w/w ethanol in water. Firstly, in in vivo tests on human hands as a skin antiseptic, results shown in Table 5A; secondly, the test formulation was assessed by the Modified Kelsey Sykes Test, results shown in Table 5B:

Formulation
(a) 1.5% w/w polymer in 65% w/w ethanol (Test)
(b) 65% w/w ethanol in water (Control)

TABLE 5A

| t(hours) | (a) (counts) | (b) (counts) |
|---|---|---|
| 0 | 11000 | 800 |
| 2 | 500 | 3100 |
| 4 | 500 | 1600 | t = 0 (before application)
t = 2, 4 (2 hrs and 4 hrs, respectively, after application and hands being gloved)

TABLE 5B

| Organism | Initial Count (cfu/mL) | Fraction Negative Tubes |
|---|---|---|
| S. Aureus | $7.0 \times 10^8$ | 5/5 |
| E. coli | $1.6 \times 10^9$ | 5/5 |
| Ps. aeruginosa | $4.6 \times 10^8$ | 5/5 |
| P. vulgaris | $1.6 \times 10^8$ | 5/5 |

EXAMPLE 6

A series of tests were conducted to examine the impact of poly(2-propenal, 2-propenoic acid) on the odours of compositions conataining phenols and/or glutaraldehyde. Results are shown in Table 6:

Solution A—1 g poly(2-propenal, 2-propenoic acid) was dissolved in 50 mL of 1% w/w sodium carbonate.

Solution B—1 g of 4-tert-amylphenol and 2 g of sodium hydroxide was dissolved in 40 mL of water.

Solution C—25% w/w glutaraidehyde in water.

TABLE 6

| Sample | 1 minute | 5 minutes |
|---|---|---|
| Solution A + Water | 15 min | little or no odour |
| Solution B + Water | 15 min | medium phenolic odour |
| Solution C + Water | 15 min | strong pungent, irritating odour |
| Solution B + Solution A | 15 min | little or no phenolic odour |
| Solution C + Solution A | 15 min | medium pungent, irritating odour |

EXAMPLE 7

A series of tests were conducted to examine any synergy between the antimicrobial activity of solutions containing poly(2-propenal, 2-propenoic acid) and EDTA and/or phenols, and/or isotniazolinones, and/or glutaraldehyde.

If the Minimum Kill Concentrations of compounds A, B, and a mixture of A and B are a, b and m, respectively, then there is synergy ("S") upon mixing A and B if a/m+b/m>1 ie. S=(a+b)/m>1 for synergy

The following solutions were tested by the Minimum Kill Concentration Test, and gave the results shown in Table 7:

TABLE 7

| | | concentrations in p.p.m. | | | | | | |
|---|---|---|---|---|---|---|---|---|
| | | S. aureus | Ps. aeruginosa | E. coli | P. vulgaris | B. cereus | C. albicans | A. niger |
| | Experiment 1 | | | | | | | |
| a | polymer | 250 | 250 | 125 | 65 | 65 | 125 | 500 |
| b | EDTA | 625 | 625 | 80 | 155 | 80 | 155 | 1250 |
| m | polymer + EDTA | 250 | 500 | 250 | 125 | 30 | 125 | 1000 |
| S | | 4 | 2 | 1 | 2 | 5 | 2 | 2 |
| | Experiment 2 | | | | | | | |
| a | polymer | 40 | 625 | | | | | |
| b | glutaraldehyde | 80 | 155 | | | | | |
| m | polymer + glutaraldehyde | <20 | 310 | | | | | |
| S | | >6 | 3 | | | | | |
| a | polymer | <10 | 625 | | | | | |

TABLE 7-continued concentrations in p.p.m.

| | | S. aureus | Ps. aeruginosa | E. coli | P. vulgaris | B. cereus | C. albicans | A. niger |
|---|---|---|---|---|---|---|---|---|
| b | phenol | 20 | >10000 | | | | | |
| m | polymer + phenol | <20 | 1250 | | | | | |
| S | | >1 | >9 | | | | | |
| a | polymer | | 625 | | | | | 625 |
| b | thiazolinone | | 1000 | | | | | 60 |
| m | polymer + thiazolinone | | 625 | | | | | 80 |
| S | | | 3 | | | | | 9 | phenol = DOWICIDE A; thiazolinone = KATHON

EXAMPLE 8

The effects of the presence of poly(2-propenal, 2-propenoic acid) on the migration of various agents across a model for skin were studied as follows. Results are shown in Table 8:

(a) poly(2-propenal, 2-propenoic acid) (0.5 g) was dissolved in polyethylene glycol 1000 (10 g) by stirring at 70° C., then sodium hydroxide micro-pellets (50 mg) were added and stirred for 2 minutes, and then octyl methoxy cinnimate (10 g; sunscreen agent) was added, followed by a mixture of the polymeric emulsifiers PEMULIN TR1 and CARBOPOL 2984 (0.5 g; equal parts) whilst maintaining the temperature at 70° C./15 minutes. This resulting composition was then poured with stirring into water (79 g; at room temperature) and then the pH adjusted to 7.

(b) The same as (a) above, except the octyl methoxy cinnimate was substituted by octyl dimethyl p-aminobenzoate.

(c) The same as (a) above, except the 1:1 mixture of polymeric emulsifiers were substituted by a 1:1 mixture of TWEEN 80 and stearic acid.

(d) The same as (a) above, except the 1:1 mixture of polymeric emulsifiers were substituted by a 1:1 mixture of TWEEN 80 and stearic acid-followed by CARBOPOL 2984 (0.25 g).

(e) The same as (a) above, except the poly(2-propenal, 2-propenoic acid) was omitted.

(f) The same as (c) above, except the poly(2-propenal, 2-propenoic acid) was omitted In a special apparatus, the samples were applied to one side of a 0.45 micron cellulose acetate membrane in contact with, on the other side, a stirred solution of ethanol. "After" 1.5 hours, the spectrum of the "ethanol" was compared with the "Before" solution of sample in the same solvent:

TABLE 8

| "yes" = exhibits max; "no" = does not | | |
|---|---|---|
| Sample | Before | After |
| octyl methoxy cinnimate | max = 310 nm | |
| octyl dimethyl p-aminobenzoate | max = 315 nm | |
| 8(a) | yes | no |
| 8(b) | yes | no |
| 8(c) | yes | no |
| 8(d) | yes | no |
| 8(e) | yes | yes |
| 8(f) | yes | yes |

EXAMPLE 9

The capacity of poly(2-propenal, 2-propenoic acid) to absorb free radicals is indicated by each of the following:

Firstly a solution of 1% w/w poly(2-propenal, 2-propenoic acid) in aqueous sodium carbonate, adjusted to pH 7.1, was treated with two successive additions of Fenton's reagent comprising 0.1% w/w ferrous sulphate (3 mL) and 30% v/v hydrogen peroxide (3 mL), and stirred; bubbles of oxygen were observed and the typical golden colour of the solution of poly(2-propenal, 2-propenoic acid), disappeared.

Secondly, the following were mixed, as shown in Table 9:

TABLE 9

| | Sample 1 | Sample 2 |
|---|---|---|
| Linseed oil (12.5 g) | yes | yes |
| Light petroleum bp 70–90° C. (25 g) | yes | yes |
| Ethanol (20 g) | no | yes |
| Polymer (0.25 g) in ethanol (20 g) | yes | no |
| Cobalt (II) acetate (1%) in ethanol (0.1 g) | yes | yes |

Yes = included in sample
No = NOT included in sample

The inhibition by the poly(2-propenal, 2-propenoic acid) of the cobalt catalysed free-radical autoxidation of the linseed oil was demonstrated by the speed of each of the samples becoming "tacky" after drawing as films upon glass, namely, sample 2>sample 1.

EXAMPLE 10

Shown in Tables 10A, 10B and 10C are results obtained for the following typical compositions derived from the present invention:

(a) poly(2-propenal, 2-propenoic acid) (18 g) was dissolved in water (528 g) containing sodium hydrogen carbonate (18 g), and then a mixture of tetrasodium EDTA (18 g) and sodium lauryl sulphate (18 g) was added, and stirring continued for 30 minutes, after which the pH was adjusted from 8.5 to 9 by the addition of sodium hydroxide micro-pellets (approximately 2 g).

(b) Part A: poly(2propenal, 2-propenoic acid) (2.7 g) was dissolved by stirring in water (63 g) containing sodium carbonate (0.9 g), DOWFAX 3B2 (2.7 g) was added and stirring continued for 15 minutes; the pH was adjusted from 9.4 to 5.1 by the addition of 10% w/w hydrochloric acid (2.5 g).

Part B: Water (27 g) containing sodium carbonate (1.35 g) and tetrasodium EDTA (2.7 g).

Part B was added to Part A, immediately before the microbiological test.

(c) poly(2-propenal, 2-propenoic acid) (2 g) was dissolved by stirring for 20 minutes in water (98 g) containing DOWICIDE A (2 g); DOWFAX 3B2 (8 g)

was added and stirring was continued for 60 minutes to give a clear solution of pH 10.5 which was then adjusted by the addition of 10% w/w hydrochloric acid (1.2 g) to a stable emulsion of pH 5.0. The antimicrobial results were obtained after aging 38° C./14 days.

TABLE 10A

Modified Kelsey Sykes Test:

| Sample | Organism | Inoculum (cfu/mL) | Fraction negative tubes |
|---|---|---|---|
| 10(a) | E. coli | $5.3 \times 10^8$ | 5/5 |
|  | S. aureus | $4.2 \times 10^8$ | 4/5 |
|  | Ps. aeruginosa | $4.5 \times 10^8$ | 5/5 |
|  | P. vulgaris | $2.7 \times 10^8$ | 5/5 |
| 10(b) | E. coli | $5.3 \times 10^8$ | 5/5 |
|  | S. aureus | $3.8 \times 10^8$ | 5/5 |
|  | Ps. aeruginosa | $4.2 \times 10^8$ | 5/5 |
|  | P. vulgaris | $3.3 \times 10^8$ | 5/5 |
| 10(c) | E. coli | $4.3 \times 10^8$ | 5/5 |
|  | S. aureus | $4.9 \times 10^8$ | 5/5 |
|  | Ps. aeruginosa | $5.8 \times 10^8$ | 5/5 |
|  | P. vulgaris | $2.8 \times 10^8$ | 5/5 |

TABLE 10B

Sporicidal Test

| Sample | Time (hours) | Fraction Negative Tube |
|---|---|---|
| 10(a) | 3 | 5/5 |
| 10(a) | 7 | 5/5 |
| 10(a) | 24 | 5/5 |

TABLE 10C

Sporicidal Efficacy Test
cfu/slide

| Sample | Control count after 72 hours incubation | Counts of samples after 72 hours incubation |
|---|---|---|
| 11(b) | $3.4 \times 10^4$ | <10 |
| 11(c) | $3.4 \times 10^4$ | <10 |

Modifications and variations such as would be apparent to the skilled addressee are considered to fall within the scope of the present invention.

What is claimed is:

1. A method for the preparation of compositions of poly(2-propenal, 2-propenoic acid) comprising the method steps of dissolving the poly(2-propenal, 2-propenoic acid) in aqueous base, adding an organic compound containing one or more hydrophobic groups, and subsequently acidifying the solution, whereby interaction between the hydrophobic groups of the organic compound and the poly(2-propenal, 2-propenoic acid) prevents precipitation of the poly(2-propenal, 2-propenoic acid) occurring at pH≧5.5 and the solution is consequently stable over a broad pH range.

2. A method according to claim 1 wherein precipitation of the poly(2-propenal, 2-propenoic acid) is prevented at pH≧3.5.

3. A method according to claim 1 wherein the organic compound is an anionic surfactant.

4. A method according to any one of claims 1 wherein one or more phenols are added to the solution of poly(2-propenal, 2-propenoic acid) prior to acidification.

5. A method according to any one of claim 1 wherein the composition containing poly(2-propenal, 2-propenoic acid) is firstly stored for a time in basic composition prior to addition of surfactant and acidification.

6. A method according to claim 1 wherein the anionic surfactant is selected from either sodium lauryl sulphate or disodium decyl (sulfophoxy) benzene sulfonate and disodium oxybis (decylsulfophenoxy) benzene sulfonate.

7. A method according to claim 1 wherein the phenol is o-phenyl-phenol.

8. A method according to claim 1 wherein the composition exhibits increased antimicrobial activity, the method comprising preparation of the poly(2-propenal, 2-propenoic acid) in the presence of air and/or oxygen, with or without inhibitor.

9. A method according to claim 1 wherein the composition, exhibits increased antimicrobial activity, the method comprising the subsequent making of the composition of poly(2-propenal, 2-propenoic acid) into a basic composition.

10. A method according to claim 1, wherein the organic compound is one or more of ethylene diamine tetra acetic acid, a lower alkanol, a phenol, isothiazolinones and glutaraldehyde, the composition exhibiting a synergistic increase in antimicrobial activity.

11. A method according to claim 1 wherein the composition further comprises phenols and/or glutaraldehyde, whereby the odour of the phenols and/or glutaraldehyde is reduced by the presence of the poly(2-propenal, 2-propenoic acid).

12. A method according to claim 1 wherein the composition exhibits reduced trans-dermal migration of low molecular weight components of the composition as a result of the presence of poly(2-propenal, 2-propenoic acid).

13. A method according to claim 12 wherein the low molecular weight composition contains a sunscreen agent.

14. A method according to claim 12 wherein the sunscreen agent is either or both of octyl methoxy cinnamate and octyl dimethyl p-aminobenzoate.

15. A method according to claim 1 wherein the composition, especially for dermatological use, exhibits a sunscreening effect as a result of the presence of poly(2-propenal, 2-propenoic acid).

16. A method according to claim 1 wherein the composition exhibits the formation of a continuous antimicrobial film on substrates.

17. A method according to claim 1 wherein the composition, especially for dermatological use exhibits a free-radical scavenging effect as the result of the presence of poly(2-propenal, 2-propenoic acid).

18. An aqueous polymeric composition comprising poly (2-propenal, 2-propenoic acid) and an organic compound containing one or more hydrophobic groups, wherein interaction between the hydrophobic groups of the organic compound and the poly(2-propenal, 2-propenoic acid) prevents the precipitation of the poly(2-propenal, 2-propenoic acid) at pH≧5.5.

19. A composition according to claim 17 wherein the poly(2-propenal, 2-propenoic acid) does not precipitate at a pH≧3.5.

20. A composition according to claim 18 wherein the organic compound is an anionic surfactant.

21. A composition according to claim 20, wherein the anionic surfactant is chosen from either sodium lauryl sulphate or disodium decyl (sulfophoxy) benzene sulfonate and disodium oxybis (decylsulfophenoxy) benzene sulfonate.

22. A composition according to claim 18 further comprising one or more phenol.

23. A composition according to claim 22 wherein the phenol is o-phenyl-phenol.

24. A composition according to claim 18 wherein the composition further comprises one or more of ethylene diamine tetra acetic acid, a lower alkanol, a phenol, isothiazolinones and glutaraldehyde, the composition exhibiting a synergistic increase in antimicrobial activity.

25. A composition according to claim 18 wherein the composition is an emulsion.

26. A method of disinfecting skin comprising applying a composition according to claim 18 to the skin to produce an antimicrobial effect.

27. A method of disinfecting an inanimate object comprising applying a composition according to claim 18 to the object to produce an antimicrobial effect.

28. A method of preparing an animal feed comprising adding a composition according to claim 18 to the animal feed.

* * * * *